US006423093B1

(12) United States Patent
Hicks et al.

(10) Patent No.: US 6,423,093 B1
(45) Date of Patent: Jul. 23, 2002

(54) METHOD OF INSERTION OF KERATOPROSTHESES

(75) Inventors: Celia R Hicks, Carlisle; Geoffrey J Crawford, Floreat; Traian V Chirila, Bentley; Ian J Constable, Mosman Park, all of (AU)

(73) Assignee: The Lions Eye Institute of Western Australia Incorporated, Nedlands (AU)

(*) Notice: Subject to any disclaimer, the term of this patent is extended or adjusted under 35 U.S.C. 154(b) by 19 days.

(21) Appl. No.: 09/626,310

(22) Filed: Jul. 26, 2000

Related U.S. Application Data

(60) Provisional application No. 60/153,809, filed on Sep. 14, 1999.

(51) Int. Cl.⁷ .................................................. A61F 2/14
(52) U.S. Cl. ...................... 623/5.11; 128/898; 623/5.15
(58) Field of Search .................. 623/4.1, 5.16; 128/898

(56) References Cited

U.S. PATENT DOCUMENTS

| | | | |
|---|---|---|---|
| 4,586,929 A | 5/1986 | Binder | 623/5 |
| 4,693,715 A | 9/1987 | Abel | 623/5 |
| 4,772,283 A | 9/1988 | White | 623/5 |
| 4,865,601 A | 9/1989 | Caldwell et al. | 623/5 |
| 4,923,466 A | 5/1990 | Pintucci | 623/5 |
| 4,932,968 A | 6/1990 | Caldwell et al. | 623/6 |
| 5,108,428 A | 4/1992 | Capecchi et al. | 623/5 |
| 5,300,115 A | 4/1994 | Py | 623/4 |
| 5,300,116 A | 4/1994 | Chirila et al. | 623/5 |
| 5,458,819 A | 10/1995 | Chirila et al. | 264/1.7 |
| 5,489,300 A | 2/1996 | Capecchi et al. | 623/5 |
| 5,489,301 A | 2/1996 | Barber | 623/5 |
| 5,713,956 A | 2/1998 | Legeais | 623/5 |
| 5,843,185 A | 12/1998 | Rolden et al. | 623/5 |

FOREIGN PATENT DOCUMENTS

| | | |
|---|---|---|
| AU | 20824/92 | 10/1994 |
| FR | 2 649 605 | 7/1989 |

*Primary Examiner*—Corrine McDermott
*Assistant Examiner*—Thomas Barrett
(74) *Attorney, Agent, or Firm*—Williams Morgan & Amerson

(57) ABSTRACT

Disclosed is a method of insertion of keratoprostheses, and in particular, a method of surgical insertion and placement of a soft hydrogel prosthetic corneal device into the host cornea. The method of the invention provides a greatly improved rate of success for the implantation and retention of the device.

11 Claims, 4 Drawing Sheets

US 6,423,093 B1

METHOD OF INSERTION OF KERATOPROSTHESES

The present application claims priority to U.S. Provisional Patent Application Ser. No. 60/153,809, filed Sep. 14, 1999, and to Australian Provisional Patent Application Serial No. PQ1878, filed Jul. 28, 1999.

FIELD OF THE INVENTION

This invention relates to a method of insertion of keratoprostheses, and in particular to a method of surgical insertion and placement of a soft hydrogel prosthetic corneal device into the host cornea. The method of the invention provides a greatly improved rate of success for the implantation and retention of the device.

BACKGROUND OF THE INVENTION

In spite of 50 years of attempts to make a functional artificial cornea (keratoprosthesis) from synthetic polymers, pathological complications following the implantation of these devices, an operation known as prosthokeratoplasty, have prevented an acceptable success rate from being achieved. Despite considerable research, there is therefore still a need in the art to improve the materials and design of keratoprosthesis.

The most devastating complication of prosthokeratoplasty, extrusion of the polymeric keratoprostheses, appears to be facilitated by the lack of biointegration between implant material and host corneal tissue.

In an attempt to overcome this problem, devices with porous skirts have been developed over the last decade. See for example U.S. Pat. No. 4,865,601 (Caldwell and Jacob-LaBarre); No. 4,923,466 (Pintucci); No. 4,932,968 (Caldwell and Jacob-LaBarre); No. 5,108,428 (Capecchi et al.); No. 5,300,115 (Py); No. 5,300,116 (Chirila et al.); No. 5,458,819 (Chirila et al.); No. 5,489,301 (Barber); No. 5,713,956 (Legeais); and No. 5,843,185 (Leon Rolden and Barraquer Granadas), French Patent No. 2,649,605 (Legeais et al.); and Australian Patent No. 650156 (Chirila et al.). After implantation, these devices are substantially incorporated into the host tissue, due to invasion and proliferation of cells into the pores of the annular peripheral zone. The results obtained in human patients using soft, flexible keratoprostheses with porous skirts appear promising, as disclosed in Caldwell, D. R., Transactions of the American Ophthalmological Society, vol. 95, pp. 751–802 (1997); "The soft keratoprosthesis"; Legeais, J. M., Renard, G., Parel, J. M., Savoldelli, M. and Pouliquen, Y., Archives of Ophthalmology, vol. 113, pp. 757–763 (1995): "Keratoprosthesis with biocolonizable microporous flurocarbon haptic"; Legeais, J. M. and Renard, G., Biomaterials, vol. 19, pp. 1517–1522 (1988): "A second generation of artificial cornea (Biokpro II)"; and Hicks, C. R., Crawford, G. J., Chirila, T. V., Lou, X., Platten, S., Vijayasekaran, S. and Constable, I. J., Proceedings, The $3^{rd}$ KPro Study Group Meeting, Birmingham, Jun. 24–26, 1999, pp. 9–10 (1999): "Pilot study of the Chirila keratoprosthesis in human patients".

Relatively few types of soft keratoprostheses have been developed to date. A review of the surgical techniques used for implantation of these devices shows that a full-thickness implantation technique, analogous to a standard penetrating keratoplasty, is normally used.

U.S. Pat. No. 4,586,929 by Binder discloses a keratoprosthesis consisting of a rigid optical cylinder screwed into a soft one-piece system composed of a support cylinder and a base plate, both made from poly(2-hydroxyethyl methacrylate) (henceforth designated as PHEMA) hydrogel. The soft portion is implanted according to a full-thickness procedure consisting of the following steps: superficial lamellar keratectomy, trephination, insertion, suturing, and coverage with the detached keratectomized corneal layer. After the trephination of the latter, the rigid optical cylinder is inserted, then sutured and covered with pretibial periosteum and conjunctiva (if available). Alternatively, in severe dry eye cases, the closed eyelid is sutured over the entire corneal surface.

U.S. Pat. No. 4,693,715 discloses a method of implantation of a PHEMA keratoprosthesis which is a conventional full-thickness procedure, similar to penetrating keratoplasty.

U.S. Pat. No. 4,772,283 by White discloses two procedures for the implantation of a soft PHEMA keratoprosthesis comprising a peripheral portion consisting of preserved (and preferably denatured) human connective tissue (cornea, sclera, cartilage etc.): (a) a conventional full-thickness technique, similar to penetrating keratoplasty; and (b) insertion into an intrastromal pocket, without removing corneal tissue or using sutures. The latter technique is suitable only for the surgical correction of refractive errors, as it is ineffective in the restoration of an irreversibly damaged cornea.

U.S. Pat. Nos. 4,865,601 and 4,932,968 by Caldwell and Jacob-LaBarre disclose a keratoprosthesis consisting of a core made of polyurethanes or silicones, joined to a radial multi-pronged skirt made of porous polytetrafluoroethylene, both portions being soft and flexible. The implantation technique is essentially a full-thickness insertion, involving the removal of the corneal button in two stages. The technique includes: central circular trephination of the cornea as deep as the Descemet's membrane; radial lamellar incision into the stroma as far as the limbus, in which radial tunnel incisions are cut extending into the sclera; placing the cornea between the walls of the central trephined incision; and placement into the tunnel incisions of the remaining skirt extensions. However, for a modified version of this prosthesis, with a polyurethane core, but a double-layered skirt made of porous polyetherurethanes, Py in U.S. Pat. No. 5,300,115 discloses a full-thickness implantation, identical to a standard penetrating keratoplasty, and stipulates it as an advantage over the previous model.

The procedure disclosed by Capecchi et al. in U.S. Pat. No. 5,489,300 for the implantation of a soft keratoprosthesis, consisting of a poly(vinyl alcohol) core and a fibrous polybutylene skirt, is substantially a full-thickness insertion, identical to penetrating keratoplasty.

Our experience with the soft, flexible PHEMA keratoprosthesis disclosed by Chirila et al. in U.S. Pat. Nos. 5,300,116 and 5,458,819 and in Australian. Patent No. 650156, has shown that the full-thickness implantation technique, analogous to a standard penetrating keratoplasty, has significant disadvantages, and may contribute to post-operative complications: See Hicks, C. R., Crawford, G. J., Chirila, T. V., Lou, X., Platten S., Vijayasekaran, S. and Constable, I. J., Proceedings, The $3^{rd}$ KPro Study Group Meeting, Birmingham, Jun. 24–26, 1999, pp. 9–10 (1999): "Pilot study of the Chirila keratoprosthesis in human patients".

This full-thickness implantation procedure relies upon the conservation of an intact conjunctival flap, which after opening over the optic, must not retract peripherally, nor enlarge centrally, so as to expose the porous skirt. When the available conjunctiva is compromised by pre-existing pathological conditions, this prerequisite is almost impossible to fulfil. Alternative tissue membranes which may be used for this purpose, such as buccal mucosa, are less satisfactory. Additionally, this procedure is dependent upon perfect perioperative and postoperative wound apposition, which is more difficult to achieve and maintain than with donor tissue. Finally, this procedure is also dependent upon a reasonable resistance to tearing of the skirt when sutured, a requirement which is difficult to fulfill, as the soft porous materials of the keratoprosthesis inherently have a low mechanical strength.

The method of insertion into, and placement within, the host cornea is an important aspect of the implantation of soft keratoprostheses. We have now surprisingly found that certain aspects of this method are critical for a successful outcome of the implantation of a soft, flexible keratoprosthesis with a porous skirt.

SUMMARY OF THE INVENTION

It is an object of this invention to provide a simple implantation procedure that assures an insertion and placement of the keratoprosthesis which minimises the risk of postoperative complications such as wound leakage and extrusion. Additional advantages of the method of the invention include one or more of the following:

(a) direct suturing of the prosthesis is not required;
(b) close apposition of the prosthetic skirt to stroma is assured;
(c) the use of a conjunctival flap is less critical, and is not essential for achieving a proper biointegration of the prosthetic rim;
(d) a longer time is available for tissue and vascular ingrowth; and
(e) less frequent follow-up and postoperative maintenance is required.

The method is applicable to any soft, flexible keratoprosthetic model with or without a porous skirt, and indeed to any soft, flexible corneal implant. Thus the invention provides a method of implanting a soft, flexible keratoprosthesis in the eye, comprising the steps of:

(a) de-epithelializing the cornea;
(b) making a 360°-circular peritomy in the conjunctiva;
(c) making a scleral incision up to the half thickness of the sclera, approximately 1 mm posterior to the superior limbus;
(d) dissecting the cornea at half thickness to create a superior semicircular corneal flap;
(e) making an inferior semicircular intrastromal pocket confined within the lamellar bed, the edge, and the anterior cornea, continuous with the plane of the dissection in the superior cornea;
(f) reflecting inferiorly and retracting the superior corneal flap;
(g) making a circular opening through the posterior corneal lamella, overlying the central visual axis;
(h) inserting the keratoprosthesis into the pocket and placing the optic core centred over the posterior corneal opening;
(i) placing the superior corneal flap over the keratoprosthesis;
(j) suturing the scleral incision;
(k) optionally, fashioning a covering flap to cover the entire surface of the globe; and subsequently
(l) making a central opening, through both the conjunctiva and the anterior corneal lamella to expose the optic of the keratoprosthesis.

Preferably the method also includes one or more of the following features:

(a) the scleral incision extends over about 160 to about 180°;
(b) the edge of the inferior intrastromal pocket is situated at a distance of about 0.5 to about 3 mm from the limbus;
(c) the circular opening through the posterior corneal lamella has a diameter between about 2 and about 5 mm; the period of time between step (j) and step (k) is between about 1 and about 5 months; and
(d) the circular opening through the covering flap and the corneal flap has a diameter between about 2 and about 5 mm.

The covering flap may be fashioned from conjunctival tissue or may alternatively be fashioned from a mucosal graft. Preferably the mucosal graft is tissue from the buccal mucosa.

It will be clearly understood that the method of the invention is applicable to any soft, flexible corneal implant, with or without a skirt.

For the purposes of this specification it will be clearly understood that the word "comprising" means "including but not limited to", and that the word "comprises" has a corresponding meaning.

DETAILED DESCRIPTION OF THE INVENTION

The invention will now be described in detail by way of reference only to the following examples, and to the accompanying drawings.

In a preferred embodiment, the method of the present invention comprises the following steps. The host cornea is de-epithelialized, and a total circular conjunctival peritomy is performed. A scleral incision as deep as the half thickness of the sclera is then made, just posterior to the superior limbus and extending over an arc of 160 to 180°. Starting from this incision, the cornea is dissected at half thickness, and a corneal flap is created in this plane extending up to the half-circle diameter. The dissection is then continued to within 0.5–3 mm of the limbus to create an inferior intrastromal pocket, continuous with the bed of the superior flap. The free superior corneal anterior lamella is reflected inferiorly and retracted gently, allowing the trephination of a circular hole through the posterior lamella of the cornea overlying the visual axis and communicating with the anterior chamber of the eye. The keratoprosthesis is then placed between the anterior and posterior lamellae, so that the transparent core lies over the circular hole. The anterior lamella is then repositioned, and the sclera is sutured. A conjunctival flap is then fashioned to cover the entire anterior surface of the eye. Both corneal and conjunctival flaps are opened by a trephination overlying the visual axis and in line with the posterior opening, in a secondary procedure which should be performed no earlier than 1 month following implantation. If a conjunctival flap cannot be created, a mucosal graft, such as buccal mucosa, can be used; however, coverage by such a flap is much less critical than in the case of full-thickness implantation. The method is illustrated in more detail in the accompanying drawings.

Figure 1:
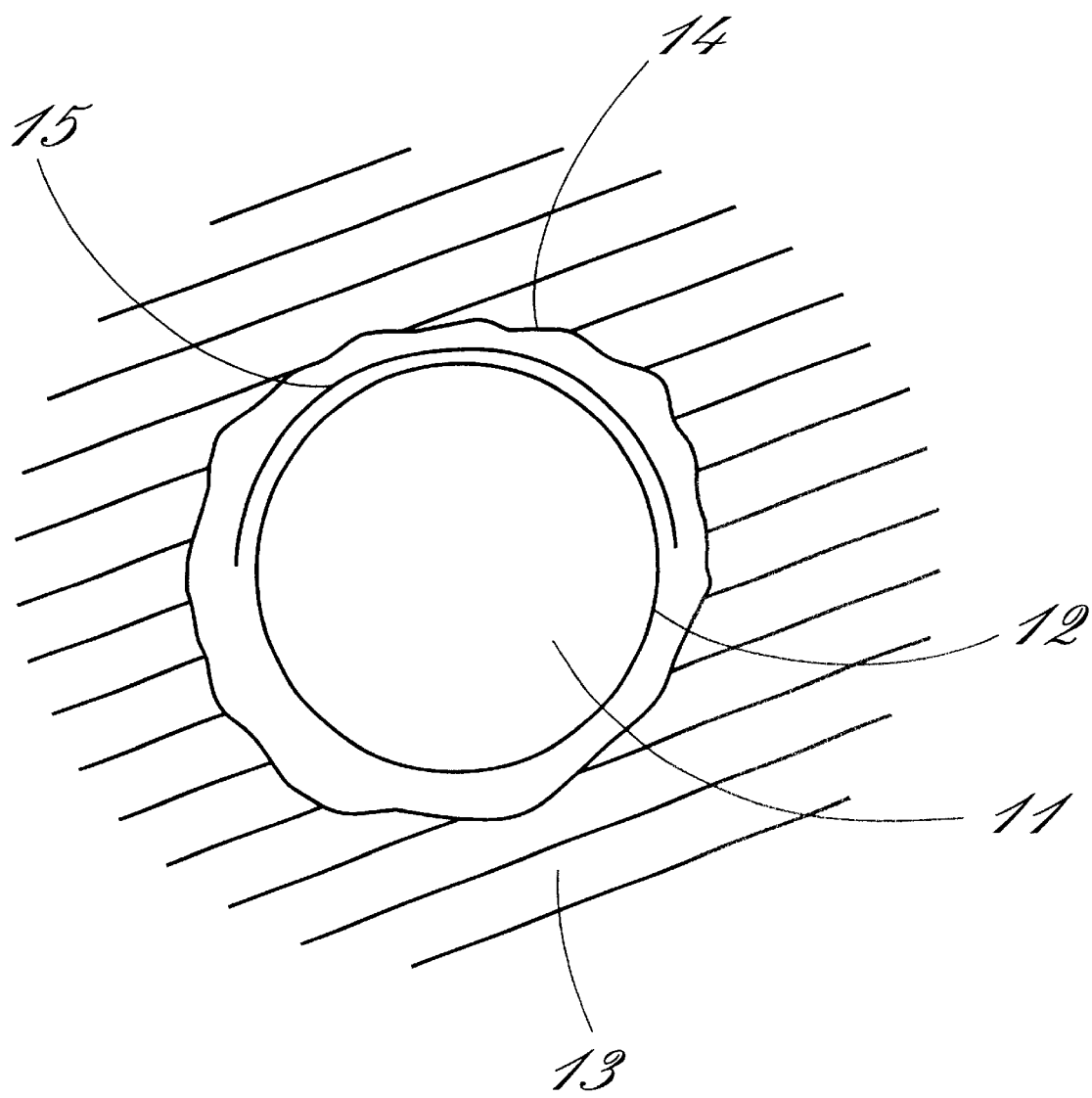
FIG. 1 is a schematic representation of the front view of the eye, showing the stages of conjunctival peritomy and scleral incision.
Figure 2:
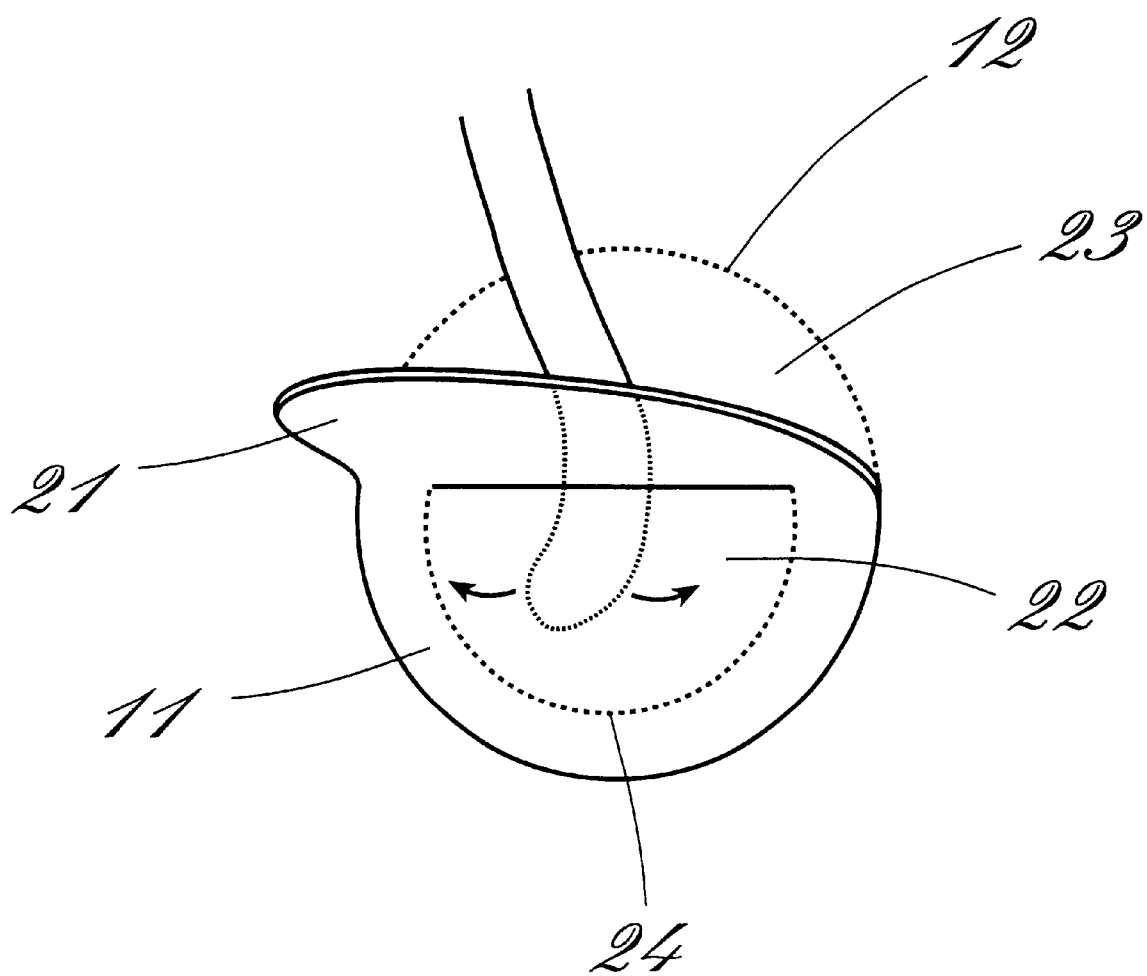
FIG. 2 is a schematic representation of the front view of the eye, showing the stages of lamellar dissection of the cornea to create a superior corneal flap and an inferior pocket.
Figure 3:
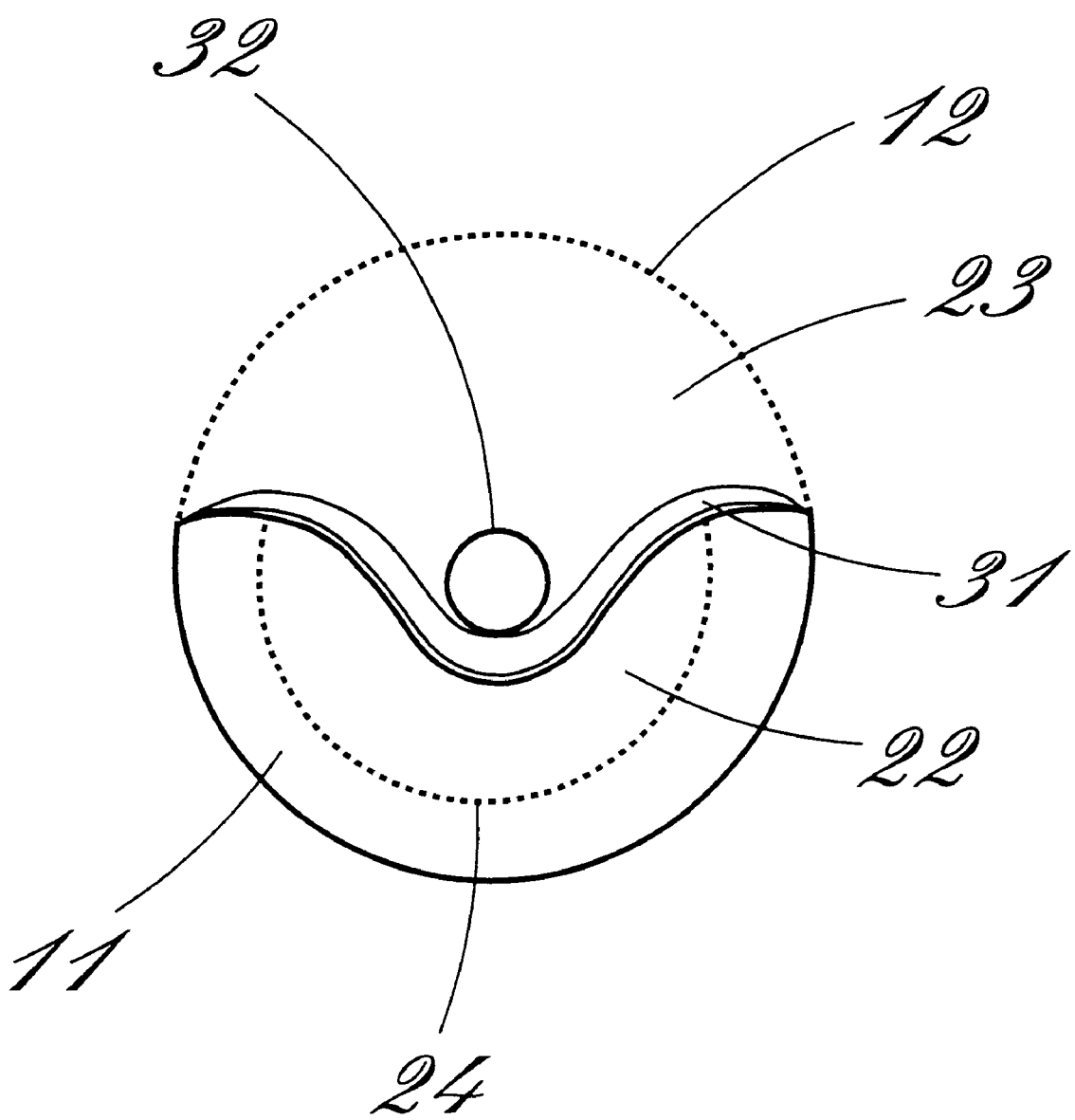
FIG. 3 is a schematic representation of the front view of the eye, showing the trephination through the posterior corneal lamella.
Figure 4:
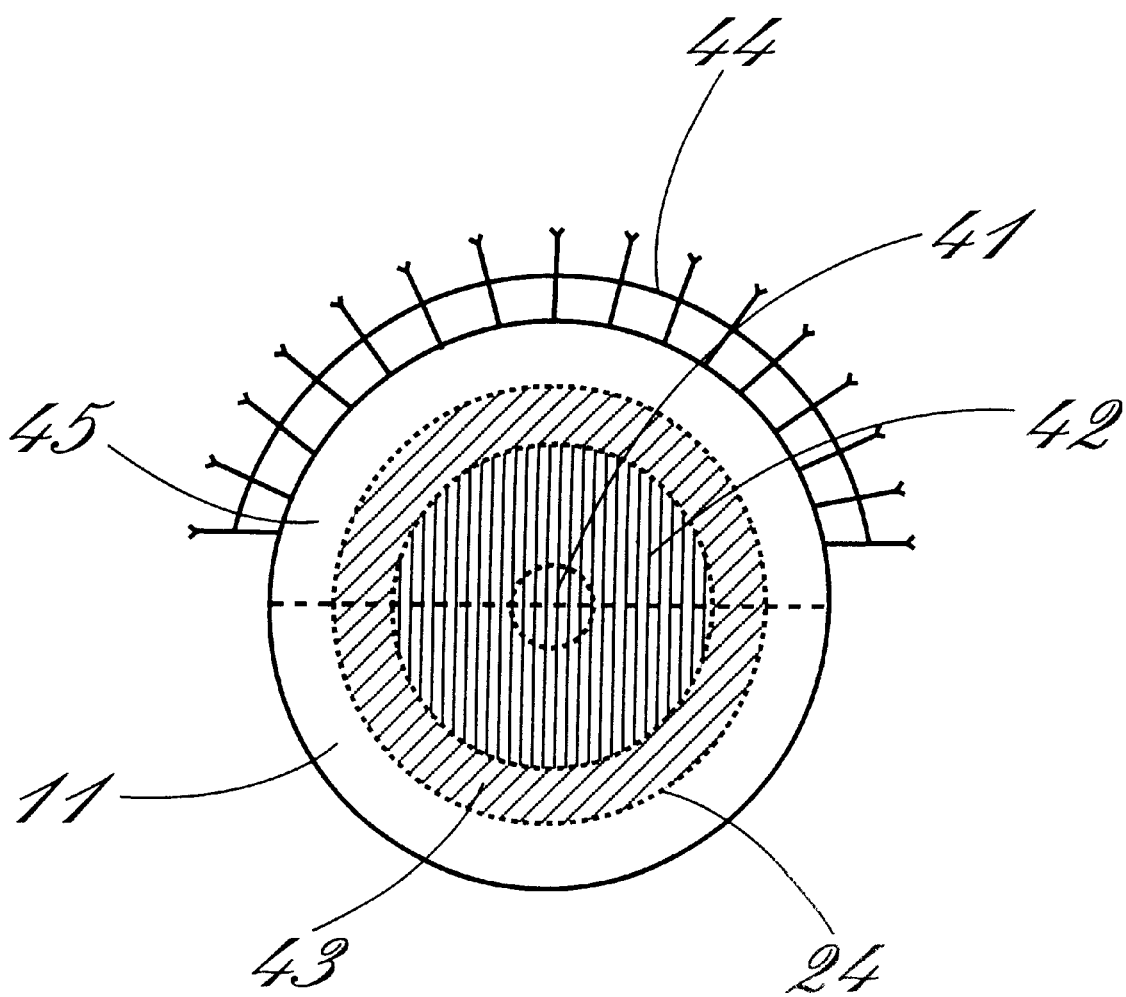
FIG. 4 is a schematic representation of the front view of the eye, showing the keratoprosthesis after placement, coverage and suturing of the limbal wound.

FIG. 1 depicts the cornea 11, limbus 12 and conjunctiva 13. The conjunctival peritomy provides the conjunctival edge 14. The scleral incision is depicted as 15. FIG. 2 depicts the corneal flap 21 and the inferior intrastromal pocket 22 created on the lamellar bed 23 and extending up to the edge 24. FIG. 3 depicts the reflected corneal flap 31 and the trephination of the opening 32 in the posterior corneal lamella. FIG. 4 depicts the placement of the keratoprosthesis (consisting of core 42 and skirt 43), covered by the corneal flap 45 and overlying the posterior opening 41. The sutured scleral incision is depicted as 44.

The preferred method for implantation of a soft, flexible keratoprosthesis is performed as follows. The patient is anaesthetised. The cornea 11 is de-epithelialized, using a knife such as a beaver blade. A circular conjunctival 360°-peritomy and dissection along the edge 14 are performed to expose the limbus 12 and perilimbal sclera, especially in the superior half of the eye, followed by haemostasis. Using a diamond knife, a half-depth scleral incision 15 is then made, approximately 1 mm posterior to the superior limbus and extending over 160 to 180°.

Starting from this incision, the cornea is dissected at half thickness, using an angled pocket knife, so as to create a flap 21, which is lifted not further than the half-circle diameter of the cornea. The dissection is continued in the same plane into the interior half of the cornea to create an inferior semicircular intrastromal pocket 22 defined within the limits of the lamellar bed 23, the edge 24 (situated at a distance of 0.5 to 3 mm from limbus), and the anterior corneal lamella 11.

The superior corneal flap 31 is then reflected inferiorly and retracted gently to allow the use of a trephine, such as a skin biopsy punch, in order to trephine a circular opening 32, 2 to 5 mm in diameter, through the posterior corneal lamella 23, overlying the central visual axis and communicating with the anterior chamber of the eye. Viscoelastics may optionally be introduced into the anterior chamber. In the aphakic eye, an anterior vitrectomy may be performed if required, through the circular opening 32.

The keratoprosthesis 42 is inserted into the pocket using an instrument such as a lens-introducing forceps with non-toothed broad flat blades, taking care not to crush or damage the prosthesis, and placed so that the optic lies centred over the opening 32 in the posterior lamella. The superior corneal flap 45 is then re-placed over the prosthesis, and the pocket 22 is closed by suturing the scleral incision 44 with 10/0 nylon sutures. If possible, a conjunctival flap, or a flap of alternative tissue, is fashioned and used to cover the entire surface of the globe.

Postoperative care should include subconjunctival administration of steroids and antibiotics at the conclusion of surgery, and topical treatment for the next two weeks, such as anti-glaucoma medication (as used preoperatively), guttae chloramphenicol and prednisolone 0.5% (4 times daily). Long-term postoperative medication, such as tetracycline 1% ointment, and freshly-made, preservative-free guttae medroxyprogesterone 1%, both 4 times daily, is required until the secondary procedure is performed.

Approximately 1 to 5 months after implantation, the conjunctival and anterior corneal covering layers are trephined to create a circular opening, 2 to 5 mm in diameter, overlying the central visual axis and in line with the posterior corneal opening. Long-term medication as disclosed above is continued indefinitely after the secondary procedure.

For reviews covering the history of prosthokeratoplasty and keratoprosthetics see: Day, R., Transactions of the American Ophthalmological Society, vol. 55, pp. 455–475 (1957): "Artificial corneal implants"; Mannis, M. J. and Krachmer, J. H., Survey of Ophthalmology, vol. 25, pp. 333–338 (1981): "Keratoplasty: a historical perspective"; Barron, B. A., "Prosthokeratoplasty", in The Cornea, Churchill Livingstone, N.Y., 1988, pp. 787–803; Leibowitz, H. M., Trinkaus-Randall, V., Tsuk, A. G. and Franzblau, C., Progress in Retinal and Eye Research, vol. 13, pp. 605–621 (1994): "Progress in the development of a synthetic cornea"; Chirila, T. V., Trends in Polymer Science, vol. 2, pp. 296–300 (1994): "Modern artificial corneas; the use of porous polymers"; Hicks, C. R., Fitton, J. H., Chirila, T. V., Crawford, G. J. and Constable, I. J., Survey of Ophthalmology, vol. 42, pp. 175–189 (1997): "Keratoprosthesis: advancing towards a true artificial cornea"; Caldwell, D. R., Transactions of the American Ophthalmological Society, vol. 95, pp. 751–802 (1997): "The soft keratoprosthesis"; Chirila, T. V. et al., Progress in Polymer Science, vol. 23, pp. 447–473 (1998): "Artificial cornea with a porous polymeric skirt"; and Brenman, K. and Parel, J. M., Anales del Instituto Barraquer (Barcelona), vol. 28 (Suppl.), pp. 187–192 (1999); "Toward a complication-free KPro. A critical review of KPro advancement since 1995".

It will be apparent to the person skilled in the art that while the invention has been described in some detail for the purposes of clarity and understanding, various modifications and alterations to the embodiments and methods described herein may be made without departing from the scope of the invention concept disclosed in this specification.

What is claimed is:

1. A method of implanting a soft, flexible keratoprosthesis in the eye, comprising the steps of:
   (a) de-epithelializing the cornea;
   (b) making a 360°-circular peritomy in the conjuctiva;
   (c) making a scleral incision up to the half thickness of the sclera, approximately 1 mm posterior to the superior limbus;
   (d) dissecting the cornea at half thickness to create a support semicircular corneal flap;
   (e) making an inferior semicircular intrastromal pocket confined within the lamellar bed, the edge of the inferior intrastromal pocket, and the anterior cornea, continous with the plane of the dissection in the superior cornea;
   (f) reflecting inferiorly and retracting the superior corneal flap;
   (g) making a circular opening through the posterior corneal lamella, overlying the central visual axis;
   (h) inserting the keratoprosthesis into the pocket and placing the optic core centred over the posterior corneal opening;
   (i) placing the superior corneal flap over the keratoprosthesis;
   (j) suturing the scleral incision;

(k) optionally, fashioning a covering flap to cover the entire surface of the globe; and (l) making a central opening, through both the conjuctiva and the anterior corneal lamella to expose the optic of the keratoprosthesis.

2. The method of claim 1, in which the scleral incision extends over about 160 to about 180°.

3. The method of claim 1, in which the edge of the inferior intrastromal pocket is situated at a distance of about 0.5 mm to about 3 mm from the limbus.

4. The method of claim 1, in which the circular opening through the posterior corneal lamella has a diameter between about 2 mm and about 5 mm.

5. The method of claim 1, in which the period of time between step (k) and step (l) is between about 1 and about 5 months.

6. The method of claim 1, in which the circular opening through the covering flap and the corneal flap has a diameter between about 2 mm and about 5 mm.

7. The method of claim 1, in which the covering flap is fashioned from conjunctival tissue.

8. The method of claim 1, in which the covering flap is fashioned from a mucosal graft.

9. The method of claim 8, in which the mucosal graft is tissue from the buccal mucosa.

10. The method of claim 1, in which the keratoprosthesis to be implanted is a soft, flexible corneal implant, with a skirt.

11. The method of claim 1, in which the keratoprosthesis to be implanted is a soft, flexible corneal implant, without a skirt.

* * * * *

UNITED STATES PATENT AND TRADEMARK OFFICE
CERTIFICATE OF CORRECTION

PATENT NO. : 6,423,093 B1
DATED : July 23, 2002
INVENTOR(S) : Hicks et al.

It is certified that error appears in the above-identified patent and that said Letters Patent is hereby corrected as shown below:

<u>Title page,</u>
Item [*] Notice, delete "19 days" and insert -- 35 days -- therefor.

Signed and Sealed this

Twelfth Day of August, 2003

JAMES E. ROGAN
*Director of the United States Patent and Trademark Office*